United States Patent [19]
Leijd

[11] Patent Number: 5,624,401
[45] Date of Patent: Apr. 29, 1997

[54] CANNULA WITH PROTECTIVE DEVICE

[75] Inventor: Nicklas Leijd, Haninge, Sweden

[73] Assignee: Bo Andersson, Madrid, Spain

[21] Appl. No.: 532,665

[22] PCT Filed: Apr. 20, 1994

[86] PCT No.: PCT/SE94/00353

§ 371 Date: Oct. 13, 1995

§ 102(e) Date: Oct. 13, 1995

[87] PCT Pub. No.: WO94/23778

PCT Pub. Date: Oct. 27, 1994

[30] Foreign Application Priority Data

Apr. 20, 1993 [SE] Sweden ................................ 9301291

[51] Int. Cl.$^6$ ........................................... A61M 5/00
[52] U.S. Cl. ........................ 604/110; 604/192; 604/263
[58] Field of Search ................................ 604/110, 187, 604/192, 263, 198

[56] References Cited

U.S. PATENT DOCUMENTS

| | | | |
|---|---|---|---|
| 3,893,608 | 7/1975 | Koenig | 604/110 X |
| 5,015,234 | 5/1991 | Jullien | |
| 5,171,229 | 12/1992 | McNeil et al. | 604/192 |
| 5,188,600 | 2/1993 | Jullien | 604/110 |
| 5,197,954 | 3/1993 | Cameron | 604/110 |

*Primary Examiner*—John D. Yasko
*Attorney, Agent, or Firm*—Nixon & Vanderhye P.C.

[57] ABSTRACT

A cannula includes a protective device mounted internally in a fixed position in the cannula chassis. The protective device includes internally a latching and locking system which functions to automatically apply the protective device to the front part, the point, of the cannula injection needle when the injection needle is retracted manually so as to separate it from the cannula chassis. When the protective device has been applied and locked firmly to the front part, the point, of the injection needle, the protective device is released from its fixed position and separated from the cannula chassis by application of an appropriate manual retroaxial pulling force. When the latching and locking process is activated, the cannula injection needle is deformed. Thus the cannula is for one-time use only, since the deformed injection needle cannot be reused.

4 Claims, 5 Drawing Sheets

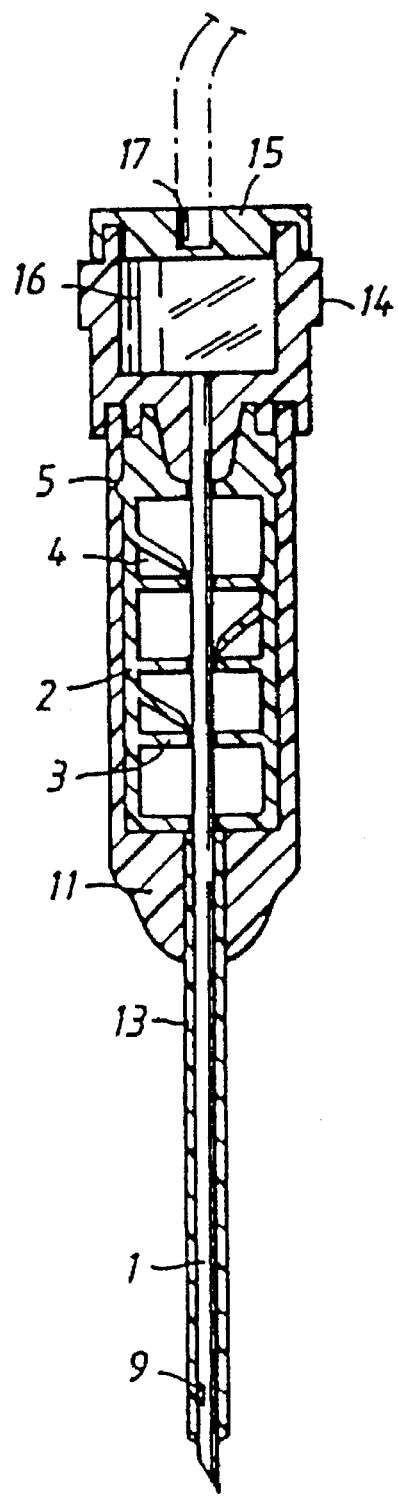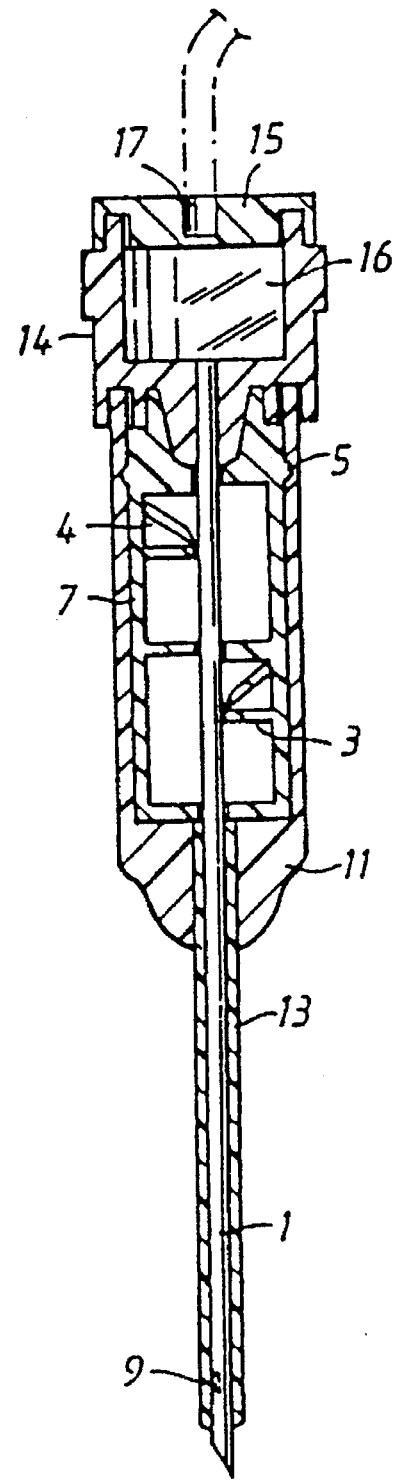

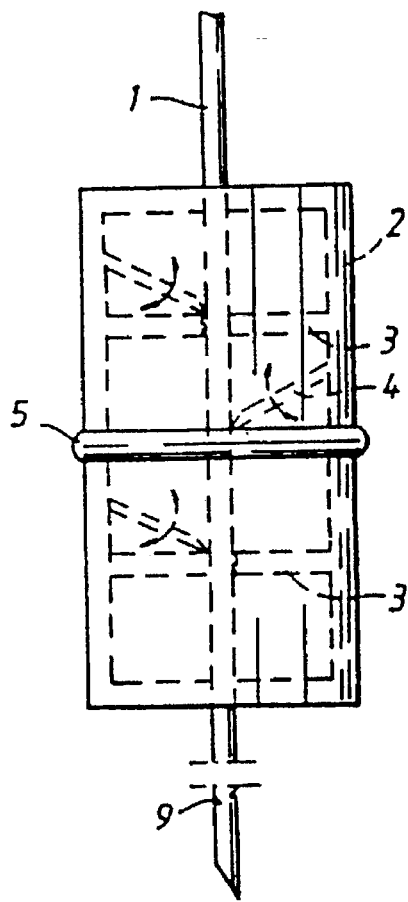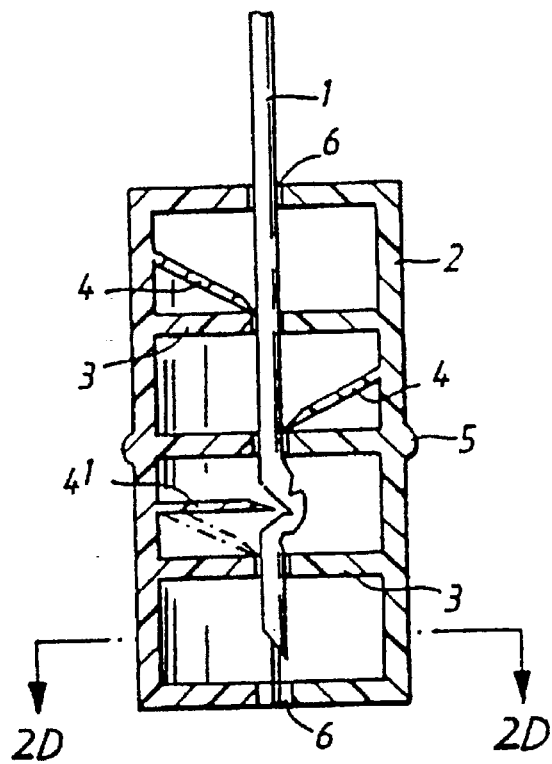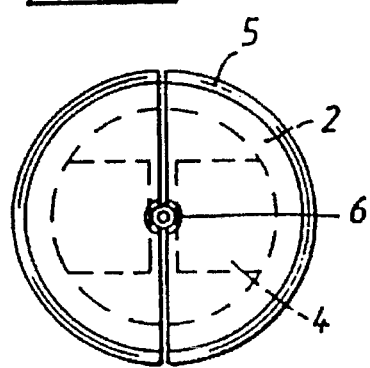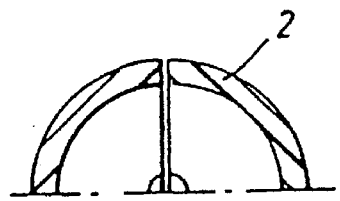

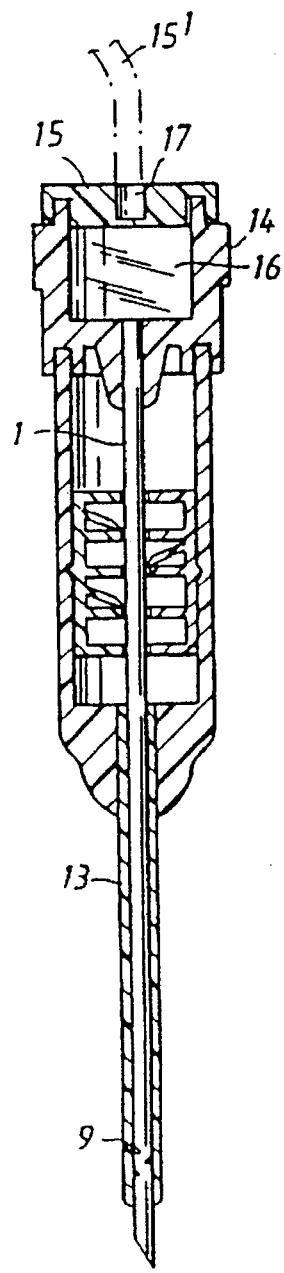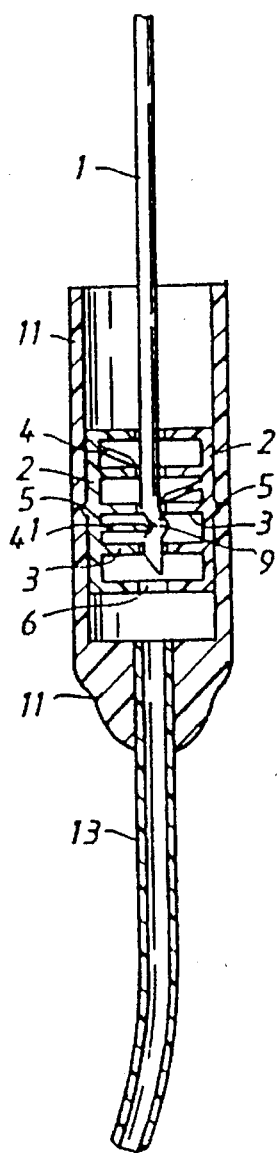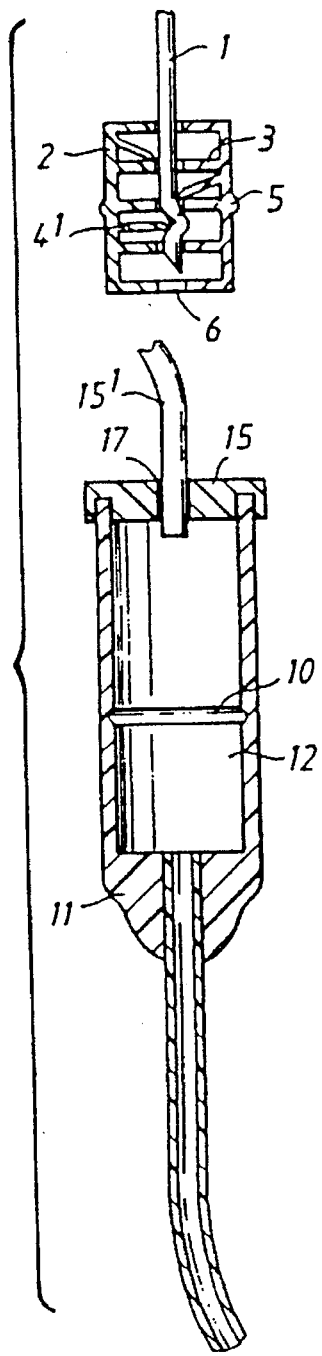

CANNULA WITH PROTECTIVE DEVICE

CROSS-REFERENCE TO RELATED APPLICATION

This application is the U.S. National Phase of PCT/SE94/00353 filed Apr. 20, 1994.

BACKGROUND AND SUMMARY OF THE INVENTION

The present invention relates to a cannula having an automatically activated protective device (protective capsule) intended for the injection needle of the cannula or hypodermic syringe. The protective device has the form of a hollow cylinder provided with two bottoms which include two central cavities, and includes an internally mounted latching and a locking system which functions to apply the protective device automatically to the forward pointed part of the injection needle when the needle is retracted or withdrawn manually so as to separate the needle from the cannula chassis. The protective device is arranged internally in the cannula chassis in a fixed position, and is released from this fixed position by means of an appropriate retroaxial pulling force, and accompanies the needle applied thereto as a protective capsule which encapsulates the point of the injection needle as the needle is separated from the chassis. The encapsulated point of the injection needle eliminates the risk of infection by "unfortunate pricking" with used, infected injection needles. The risk entailed by reusing the injection needle is eliminated, since the needle is deformed upon activation of the latching and locking process.

Those cannula or hypodermic syringes at present available commercially constitute a risk as a result of their construction and design, this risk being particularly applicable to nursing personnel who during their work are liable to "unfortunately prick themselves" with used, infected injection needles, with extremely serious consequences.

The irresponsible reuse of injection needles can occur. The described invention eliminates the above-mentioned risks.

The object of the invention is to provide for the comfort and, primarily, the safety of those who handle cannula or hypodermic syringes and to render irresponsible reuse of infected injection needles impossible. The object is to provide a cannula with a protective device on the point of the injection needle. The protective device is mounted internally of the cannula chassis, in a fixed position, and can be released from this fixed position by means of an appropriate retroaxial pulling force, wherewith the protective device accompanies this movement while seated on the front part of the injection needle, where the protective device is locked firmly to the point of the injection needle by latching and locking means as the injection needle is separated from the cannula chassis. The invention thus relates to a cannula intended for one-time use only, since the cannula—the injection needle—is deformed upon activation of the latching and locking mechanism. The invention is activated by means of cooperation between retroaxial displacement of the injection needle—perforations provided at the front part of the injection needle, the point—where latching flaps provided internally of the protective device hook firmly when the latching and locking mechanism is activated, resulting in secure and stable encapsulation of the front part, the point, of the injection needle by the protective device.

BRIEF DESCRIPTION OF THE DRAWINGS

The invention will now be described in more detail with reference to an exemplifying embodiment thereof and also with reference to the accompanying drawings, in which FIG. 1A is a schematic, longitudinal section view of a first embodiment of an inventive cannula provided with a protective device;

FIG. 1B is a schematic, longitudinal section view of a second exemplifying embodiment of an inventive cannula provided with a protective device;

FIG. 2A is a schematic side view illustration of one part of a cannula having a protective device in said first embodiment of the invention, and FIG. 2B is an end view of said first embodiment;

FIG. 2C is a schematic, longitudinal section view of a cannula provided with a protective device according to the first embodiment of the invention, and shows the latching and locking mechanism activated, and FIG. 2D is a partial cross-sectional view taken along lines 2D—2D of FIG. 2C;

FIGS. 5A–5C is a schematic, longitudinal section view of the cannula having an internally arranged protective device according to the first embodiment of the invention, and shows the protective device in three different positions; in which FIG. 5A shows the cannula and protective device disposed in a fixed appropriate position;

FIG. 5B shows the cannula and protective device with the cannula injection needle retracted axially, and shows internal latching and locking system activated;

FIG. 5C illustrates the cannula with the protective device separated from the cannula. Flexible inlet or outlet tubes are provided in the "rear cap" of the cannula, the cannula is prepared for the intended function.

DETAILED DESCRIPTION OF THE DRAWINGS

Figure 3A:
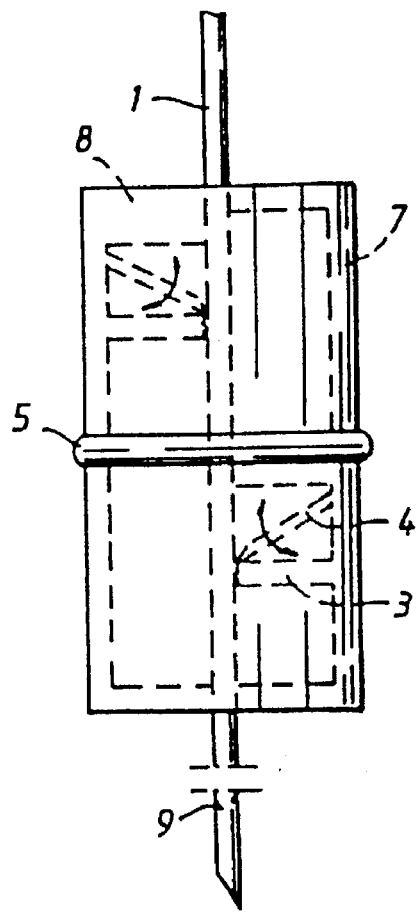
FIG. 3A is a schematic side view illustration of part of the cannula provided with a protective device according to the second embodiment of the invention.
Figure 3B:
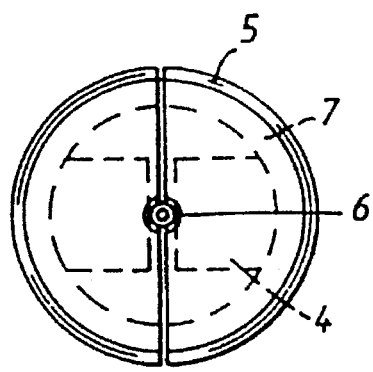
FIG. 3B is an end view of the second embodiment.

The reference numeral 1 identifies part of the cannula in which the injection needle can be moved and the purpose of which is to perforate the body and permit the body to be penetrated by a flexible plastic tube 13, which is provided at the outer circumference of the injection needle 1 so as to leave solely the point protruding and free. The injection needle 1 provides adequate support, stability, to the flexible plastic tube 13 for penetration thereof into the body.

The reference numeral 2 identifies the chassis of a protective device adjacent the injection needle 1, which is in the form of a hollow cylinder having two bottoms provided with a centrally located hollow cavity 6, and internally mounted latching and locking system for applying the protective device to the front part, the point, of the injection needle 1 (chassis 2 is manufactured in two different units for technical reasons, these two units being joined together, although this is not shown in the drawings).

The reference numeral 3 identifies support flanges provided internally in the chassis 2, the purpose of which is to centralize the injection needle 1 and to provide adequate support when the injection needle 1 is deformed upon activation of a latching flap 4 (FIG. 2C, 41).

The reference numeral 4 identifies latching flaps provided internally in the chassis 2 and intended to permit forward displacement of the injection needle 1 (see FIG. 2A), but to activate a latching and locking system when the injection needle 1 is retracted manually in an axial direction, such that the latching flap 4 will hook firmly to a vertical surface 9' which is present on the forward part of the injection needle 1. An active latching and locking process results in deformation and locking of the injection needle 1 in a fixed position at the chassis 2 of the protective device (see FIG. 2C).

The reference numeral 5 identifies a position fixing ring which is provided on the outer circumference of the chassis 2 and by means of which the protective device is guaranteed an appropriate position internally of the cannula.

The reference numeral 6 identifies two centrally located cavities at the two hollow cylindrical bottoms of the chassis 2 by means of which the injection needle 1 is stabilized and centralized.

The reference numeral 7 identifies the chassis of the protective device at the injection needle 1 in accordance with the second embodiment of the invention (for technical reasons, the chassis 7 has been manufactured in two different units which are later joined together, although this is not shown in the drawings).

Figure 3C:
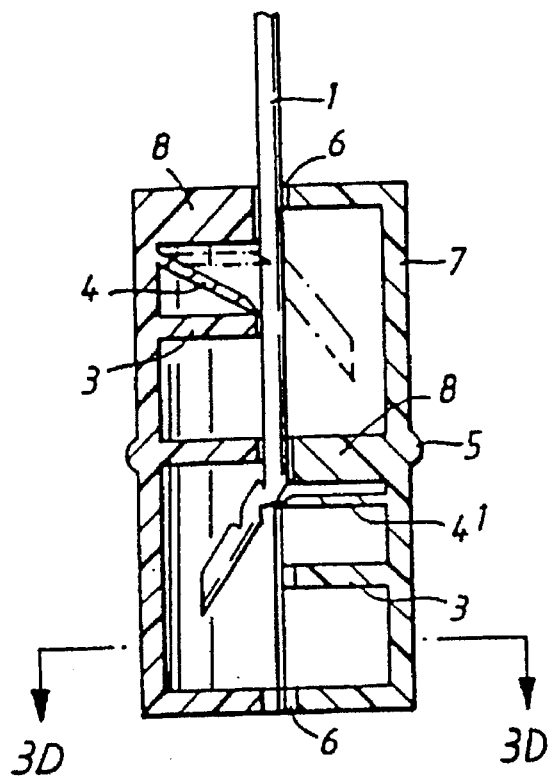
FIG. 3C is a schematic, longitudinal section view of a cannula provided with a protective device in accordance with the second embodiment of the invention, with the latching and locking mechanism activated.
Figure 3D:
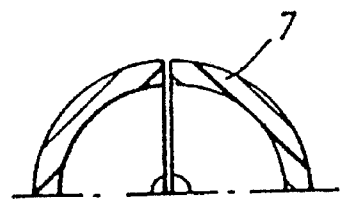
FIG. 3D is a partial cross-sectional view taken along lines 3D—3D of FIG. 3C.
Figure 4:
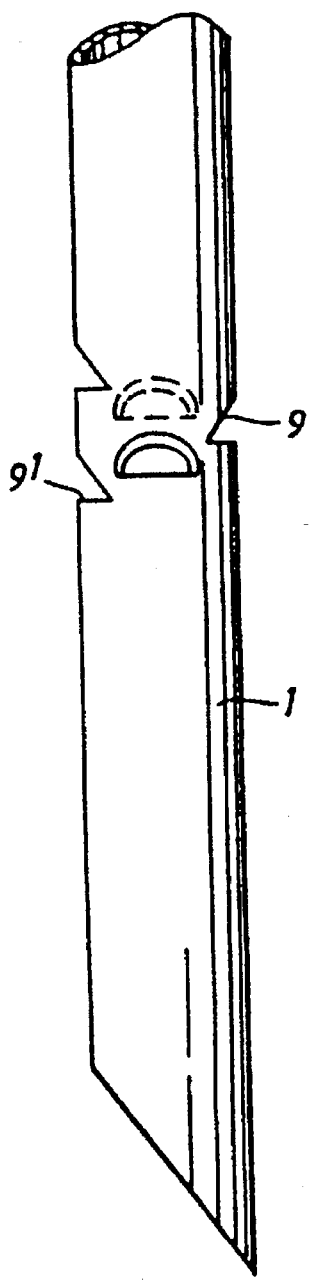
FIG. 4 illustrates schematically a plurality of axially and radially separated perforations provided at the front pan, the point, of the injection needle.

The reference numeral 8 identifies a support flange internally of a part of the chassis 7, wherein the support flange 8 coacts with the latching flap 4 in deforming and locking the injection needle 1 (see FIG. 3C).

The reference numeral 9 identifies a plurality of axially and radially separated perforations located on the outer circumference of the front part of the injection needle 1. The triangular perforations 9 are intended to allow the injection needle to move forwards, but when the injection needle 1 is withdrawn axially and the perforations 9 reach the action radius of the latching flap 4, the flap is activated and hooks firmly onto the vertical perforated surface 9' located at the outer circumference of the front part of the injection needle 1. By means of coaction—cannula—axial retraction or withdrawal of the injection needle 1 plus the perforations 9 plus latching flap 4, the latching and locking system of the protective device is activated and the injection needle 1 is deformed and locked firmly in a fixed position (see FIG. 2C).

The reference numeral 10 identifies a concave circular space located internally of the cannula, the purpose of said space being to fix the chassis 2 and 7 in an appropriately fixed position in the cylindrical internal space 12 of the cannula.

The reference numeral 11 identifies the cannula chassis.

The reference numeral 12 identifies the cylindrical internal space present in the cannula.

The reference numeral 13 identifies a flexible plastic tube applied to the cannula chassis 11.

The reference numeral 14 identifies a cap appendage firmly fixed to the rear part of the injection needle 1, the cap appendage 14 being transparent to permit the arrival of blood to be visually discerned.

The reference numeral 15 identifies a cap provided on the rear part of the cannula chassis 11.

The reference numeral 16 identifies a space formed at the cap appendage 14, to enable the arrival of blood to be visually discerned.

The reference numeral 17 identifies a hollow space formed centrally adjacent the cap 15, the purpose of this space being intended to facilitate the application of a flexible plastic tube 151 through which liquid is introduced or removed.

The reference numeral 18 identifies a formed space present internally in the cannula.

Figure 6:
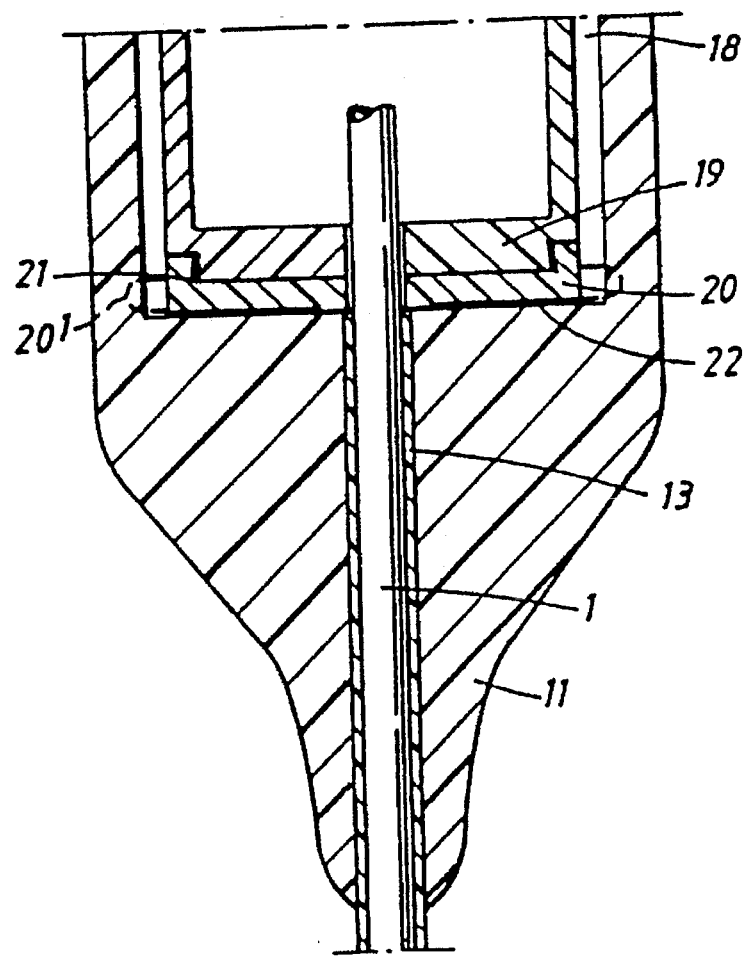
FIG. 6 is a schematic, longitudinal section view of the cannula and protective device according to a third embodiment of the invention.

The reference numeral 19 identifies the chassis of the protective device adjacent the injection needle 1, according to a third embodiment of the invention. The chassis 19 has a hollow cylindrical shape with two bottoms having centrally located hollow cavities 6, and an internal latching and locking system is provided for putting the protective device onto the front part, the point, of the injection needle 1. The lower hollow cylindrical bottom of the chassis 19 has the form of a truncated cone and is force-fitted into the circular plate 20 which has corresponding inclination (see FIG. 6, 21) and the chassis has only adequate axial withdrawal effect to release the chassis 19 from the internal circular plate 20 fixedly mounted in the front part of the cannula. The internally mounted latching and locking system of the chassis is activated first by means of manual retromovement of the injection needle 1 when the chassis 19 is locked firmly in a fixed position at the front part of the injection needle 1 as a protective capsule, whereas continued appropriate manual retroaxial pulling force will cause the separating process of the fixing device to function and the point of the injection needle 1 encapsulated by the chassis 19 is separated from the cannula chassis 11. (See FIGS. 5A, B, C). The third embodiment of the invention is mainly characterized in that the protective device is provided internally with an adhesive substance at the forward frontal area of the cannula chassis 11 and is thus not dependent on the external dimension, nor yet on any particular fixating system.

The reference numeral 20 identifies a circular part which is fixedly mounted to the forward frontal area of the cannula chassis 11 by means of an adhesive. The part 20 having an internal circular inclination 21 for its application to the front part of the chassis 19 where a similar inclination is found. The part 20 may also be applied in an appropriate position by means of a fixating system 201 provided internally in the cannula chassis 11.

The reference numeral 21 identifies a similar inclination on the front part of the chassis 19 and internally of the part 20.

The reference numeral 22 identifies the planar surface present on the circular part 20 with existing glue or paste to enable adhesive application of the protective device at the forward frontal area of the cannula chassis 11.

I claim:

1. A cannula comprising internally in a fixed position in the front part of the cannula chassis an automatically functioning protective device (protective capsule) for the point of the cannula injection needle, said protective device having a hollow cylindrical construction and including two bottoms each having a respective hollow space and including internally a latching and locking system which by application of the protective device protectively encapsulates the injection needle during the process of separating the needle from the cannula, characterized in that the protective device includes internally radially functioning latching flaps which are constructed to permit forward movement of the injection needle but which when the needle is retracted manually hook firmly to a vertical surface forming part of perforations on the front part of the needle, so that the needle will be deformed and locked firmly in a fixed position in the protective device, which accompanies the needle as the needle is separated from the cannula chassis.

2. A cannula according to claim 1, characterized by a plurality of axially and radially separate perforations provided on the front part of the injection needle, wherein the purpose of said perforations is to permit forward movement of the injection needle, wherein when the injection needle is retracted or withdrawn axially and the perforations reach the action radius of the radially acting latching flap, the latching and locking system located internally in the cannula protective device is automatically activated.

3. A cannula according to claim 1, characterized in that the internally arranged cannula protective device is disparate, and the injection needle is bent axially and deformed.

4. A cannula according to claim 1 wherein the protective device of the cannula is disparate in construction, and the front part lower bottom has the shape of a truncated cone onto which there is force fit a circular sub-part having internally a similar inclination to said truncated cone, the sub-part having a planar surface on which glue or paste is disposed to enable the protective device to be applied adhesively to the inner forward frontal area of the cannula chassis, so that the cannula chassis and the sub-part are separated by applying an appropriate retroaxial pulling force, and wherein when the protective device is adhered to the inner forward frontal area of the cannula chassis the protective device is not dependent on precise dimensions nor on a separate fixating system.

* * * * *